United States Patent
Ueda et al.

(10) Patent No.: US 7,344,048 B2
(45) Date of Patent: Mar. 18, 2008

(54) DISPENSING DEVICE AND ANALYZING APPARATUS

(75) Inventors: Makoto Ueda, Kakogawa (JP);
Kazuyuki Sakurai, Shiojiri (JP);
Hiroaki Tobimatsu, Kobe (JP)

(73) Assignee: Sysmex Corporation, Kobe-shi (JP)

(*) Notice: Subject to any disclaimer, the term of this patent is extended or adjusted under 35 U.S.C. 154(b) by 449 days.

(21) Appl. No.: 11/040,961

(22) Filed: Jan. 21, 2005

(65) Prior Publication Data

US 2005/0194394 A1    Sep. 8, 2005

(30) Foreign Application Priority Data

Jan. 22, 2004   (JP) .............................. 2004-013914

(51) Int. Cl.
*G07F 11/00* (2006.01)
(52) U.S. Cl. .......................... 221/4; 438/50; 257/718; 422/50; 422/68.1; 221/112; 221/147; 221/98
(58) Field of Classification Search ............ 438/50–53, 438/118; 257/718, 719, 415; 221/4
See application file for complete search history.

(56) References Cited

U.S. PATENT DOCUMENTS 5,406,699 A * 4/1995 Oyama ..................... 29/827

6,410,278 B1   6/2002 Notomi et al.
2003/0137080 A1* 7/2003 Bouras et al. ......... 264/272.11

FOREIGN PATENT DOCUMENTS

| JP | 03-183958 | 8/1991 |
|---|---|---|
| JP | 10-038896 | 2/1998 |
| JP | 10-246690 | 9/1998 |
| JP | 2003-344427 A | 12/2003 |

OTHER PUBLICATIONS

European Search Report for Application No. 05001106.3 Dated Mar. 21, 2006.

* cited by examiner

*Primary Examiner*—Michael Lebentritt
*Assistant Examiner*—Abdulfattah Mustapha
(74) *Attorney, Agent, or Firm*—Brinks Hofer Gilson & Lione

(57) ABSTRACT

A dispensing device is described that comprises a base, a chip attaching member which is provided movably with respect to the base and to which a dispensing chip is attached removably, a first elastic member for suppressing a movement of the chip attaching member with respect to the base, a second elastic member serving to suppress the movement of the chip attaching member with respect to the base and having a greater elastic constant than an elastic constant of the first elastic member and a detector for detecting that the chip attaching member is moved with respect to the base. An analyzing apparatus is also described.

10 Claims, 15 Drawing Sheets

DISPENSING DEVICE AND ANALYZING APPARATUS

This application claims priority under 35 U.S.C. §119 to Japanese Patent Application No. 2004-013914 filed Jan. 22, 2004, the entire content of which is hereby incorporated by reference.

FIELD OF THE INVENTION

The present invention relates to a dispensing device and an analyzing apparatus comprising the same, and more particularly to a dispensing device including a chip attaching member to which a dispensing chip is attached and an analyzing apparatus comprising the same.

BACKGROUND

Conventionally, there has been known a dispensing device including a chip attaching member to which a dispensing chip is attached (for example, see Japanese Laid-Open Patent Publication No. 2003-344427).

The Japanese Laid-Open Patent Publication No. 2003-344427 has disclosed a dispensing device in which the chip attaching member can be moved in a downward direction and a spring for energizing the chip attaching member in the downward direction is provided. In the dispensing device, when the chip attaching member is moved in the downward direction and the tip of the chip attaching member comes in contact with the bottom face of a well accommodating a liquid sample, the shock of the contact is relieved by the spring. Moreover, the dispensing device detects the amount of a movement when the chip attaching member is moved in an upward direction against the energizing force of the spring in the collision of the chip attaching member, thereby detecting the contact of the chip attaching member with the bottom face of the well.

In the dispensing device disclosed in the Japanese Laid-Open Patent Publication No. 2003-344427, in order to enhance precision in the detection of the contact of the chip attaching member, it is necessary to reduce the elastic force (energizing force) of the spring in such a manner that the chip attaching member can be moved in the upward direction against the energizing force (elastic force) of the spring also when the chip attaching member comes in contact with a dispensing chip by a very small force. If the elastic force of the spring is reduced, however, there is a problem in that a cushion effect (a shock absorbing effect) for relieving a shock cannot be sufficiently maintained when the chip attaching member is to be pressed into the dispensing chip in some cases in which an operation for bringing the chip attaching member down and pressing the chip attaching member into the dispensing chip to attach the dispensing chip to the chip attaching member is carried out.

BRIEF SUMMARY

The scope of the present invention is defined solely by the appended claims, and is not affected to any degree by the statements within this summary.

It is an object of the present invention to provide a dispensing device and an analyzing apparatus which can detect the contact of a chip attaching member with high precision, and furthermore, can sufficiently relieve a shock when a dispensing chip comes in contact with the chip attaching member.

The first aspect of the present invention relates to a dispensing device comprising a base; a chip attaching member which is provided movably with respect to the base and to which a dispensing chip is attached removably; a first elastic member for suppressing a movement of the chip attaching member with respect to the base; a second elastic member serving to suppress the movement of the chip attaching member with respect to the base and having a greater elastic constant than an elastic constant of the first elastic member; and a detector for detecting that the chip attaching member is moved with respect to the base.

The second aspect of the present invention relates to a dispensing device comprising a base which can be moved in a first direction; a chip attaching member which is provided movably in a second direction to be an opposite direction to the first direction with respect to the base and to which a dispensing chip is attached by a movement of the base in the first direction; first energizing means for giving a first energizing force directed at the first direction to the chip attaching member; second energizing means for giving a second energizing force directed at the first direction to the chip attaching member, the second energizing force being greater than the first energizing force; and a detector for detecting that the chip attaching member is moved in the second direction with respect to the base.

The third aspect of the present invention relates to a dispensing device comprising a base which can be moved in a first direction; a chip attaching member which is provided movably by a predetermined moving range in a second direction to be an opposite direction to the first direction with respect to the base and to which a dispensing chip is attached by a movement of the base in the first direction; effort applying means for applying an effort in the first direction to the chip attaching member and changing a magnitude of the effort in the middle of the movement in the second direction of the chip attaching member when the chip attaching member is to be moved in the second direction; and a detector for detecting that the chip attaching member is moved in the second direction with respect to the base.

The fourth aspect of the present invention relates to an analyzing apparatus comprising a base; a chip attaching member which is provided movably with respect to the base and to which a dispensing chip is attached removably; a first elastic member for suppressing a movement of the chip attaching member with respect to the base; a second elastic member serving to suppress the movement of the chip attaching member with respect to the base and having a greater elastic constant than an elastic constant of the first elastic member; and a detector for detecting that the chip attaching member is moved with respect to the base.

DETAILED DESCRIPTION OF THE EMBODIMENT

An embodiment of the present invention will be described below with reference to the drawings.

Figure 1:
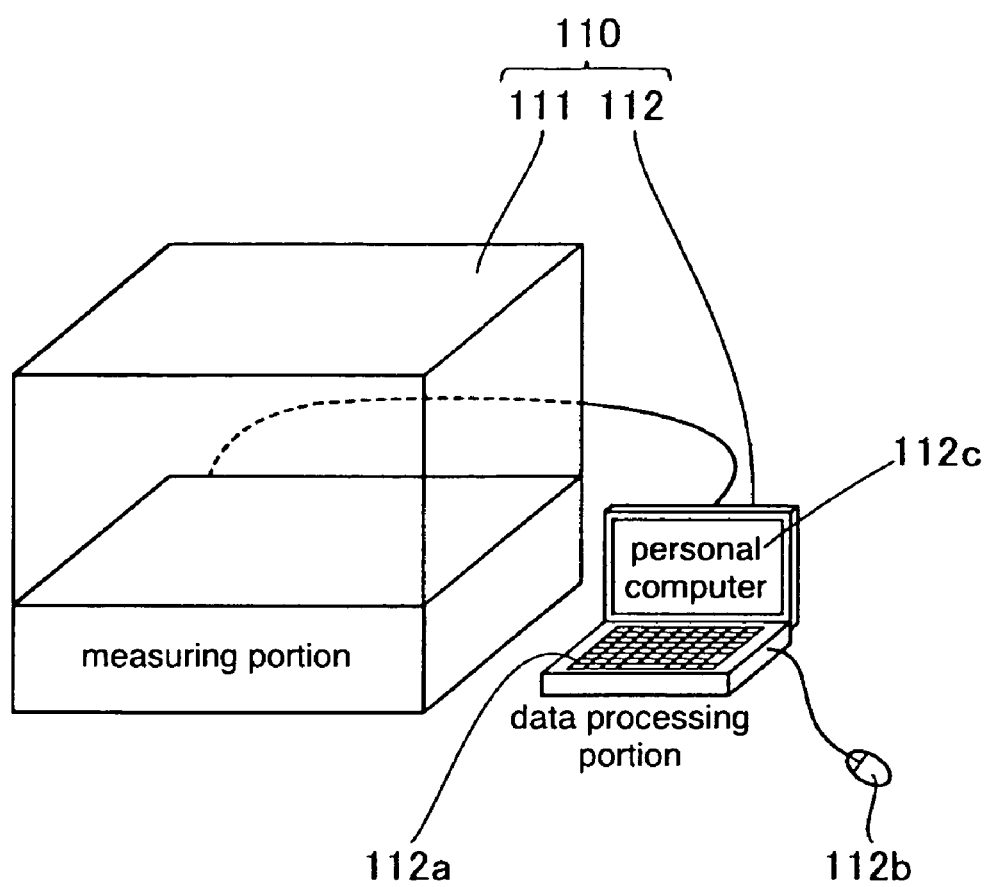
FIG. 1 is a perspective view showing the whole structures of an analyzing apparatus (a gene amplification detecting apparatus) and a data processing portion thereof according to an embodiment of the present invention.
Figure 2:
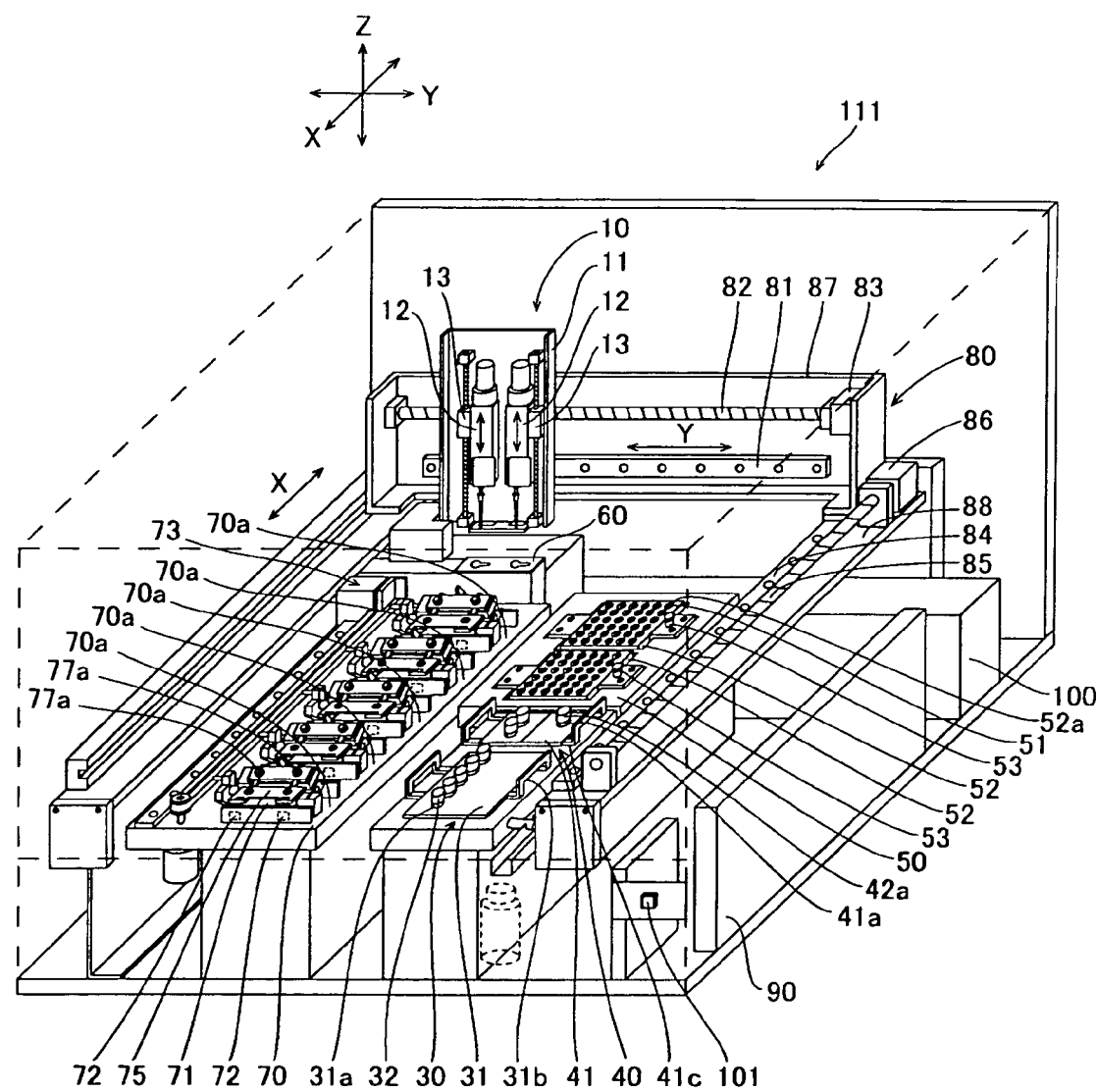
FIG. 2 is a perspective view showing the whole structure of the measuring portion of the analyzing apparatus according to the embodiment illustrated in FIG. 1.
Figure 3:
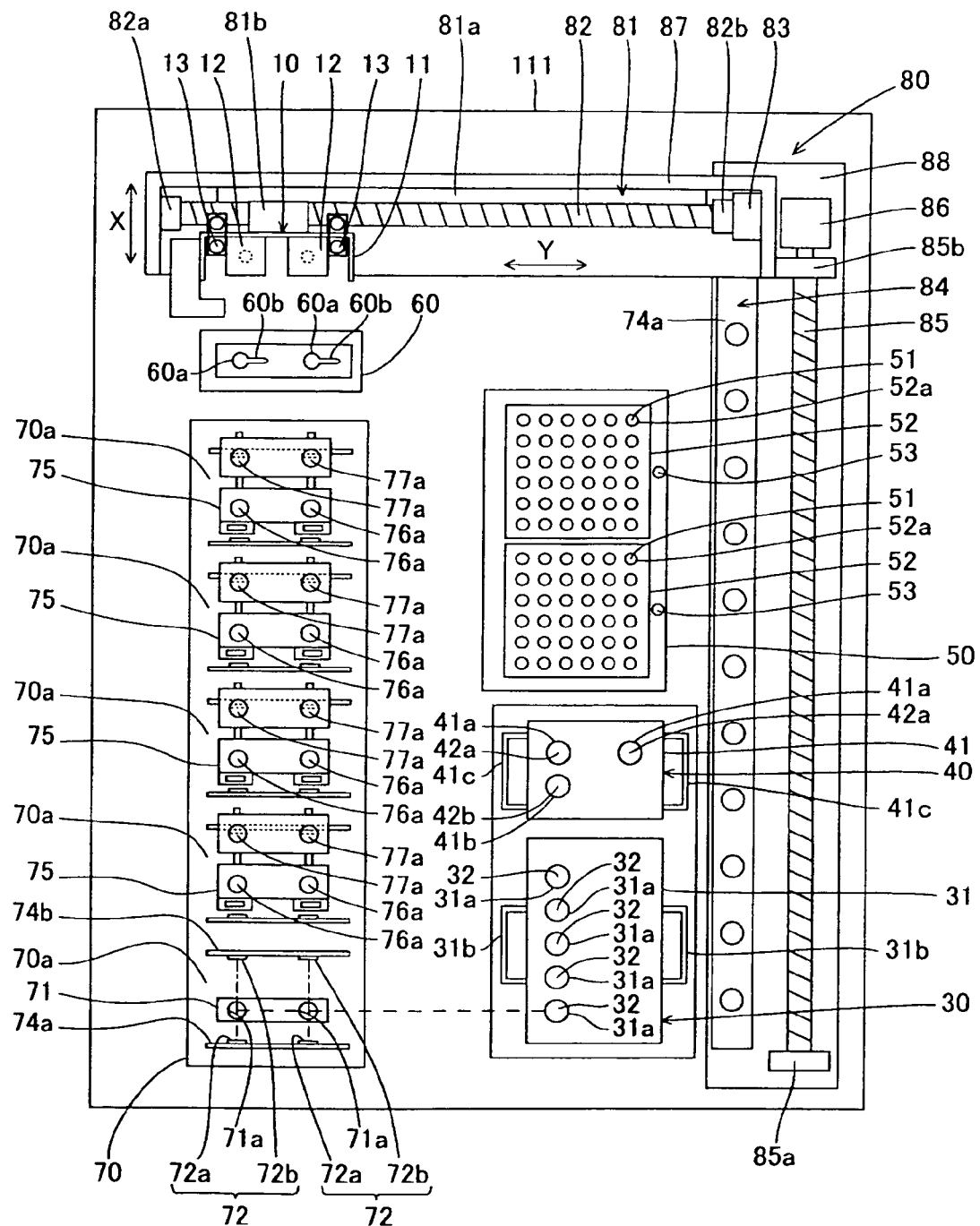
FIG. 3 is a schematic plan view showing the measuring portion of the analyzing apparatus according to the embodiment illustrated in FIG. 2.
Figure 4:
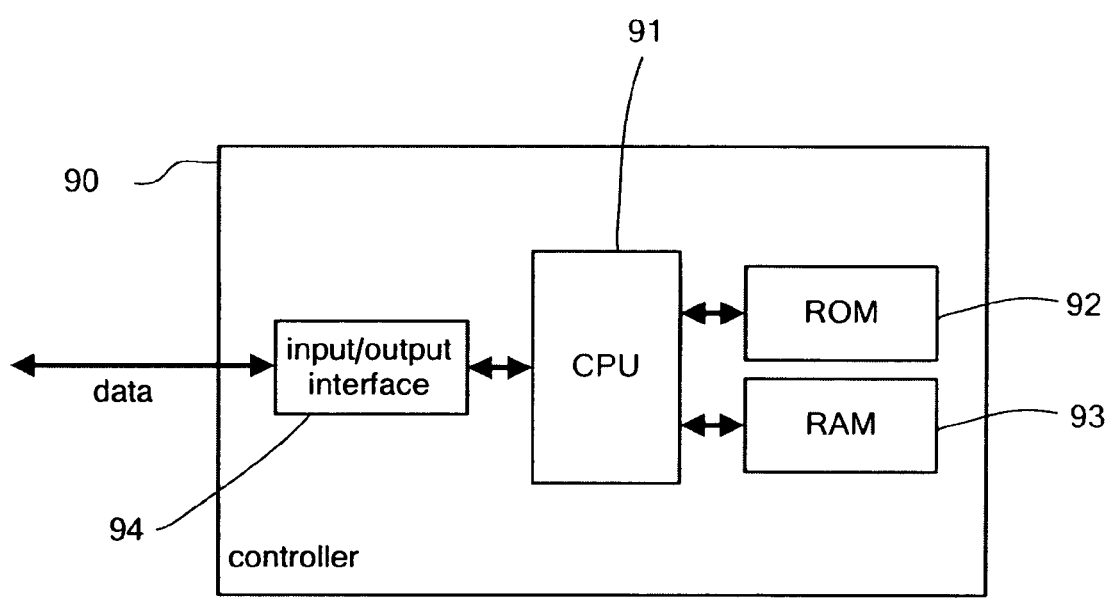
FIG. 4 is a block diagram showing the structure of a controller illustrated in FIG. 2.
Figure 5:
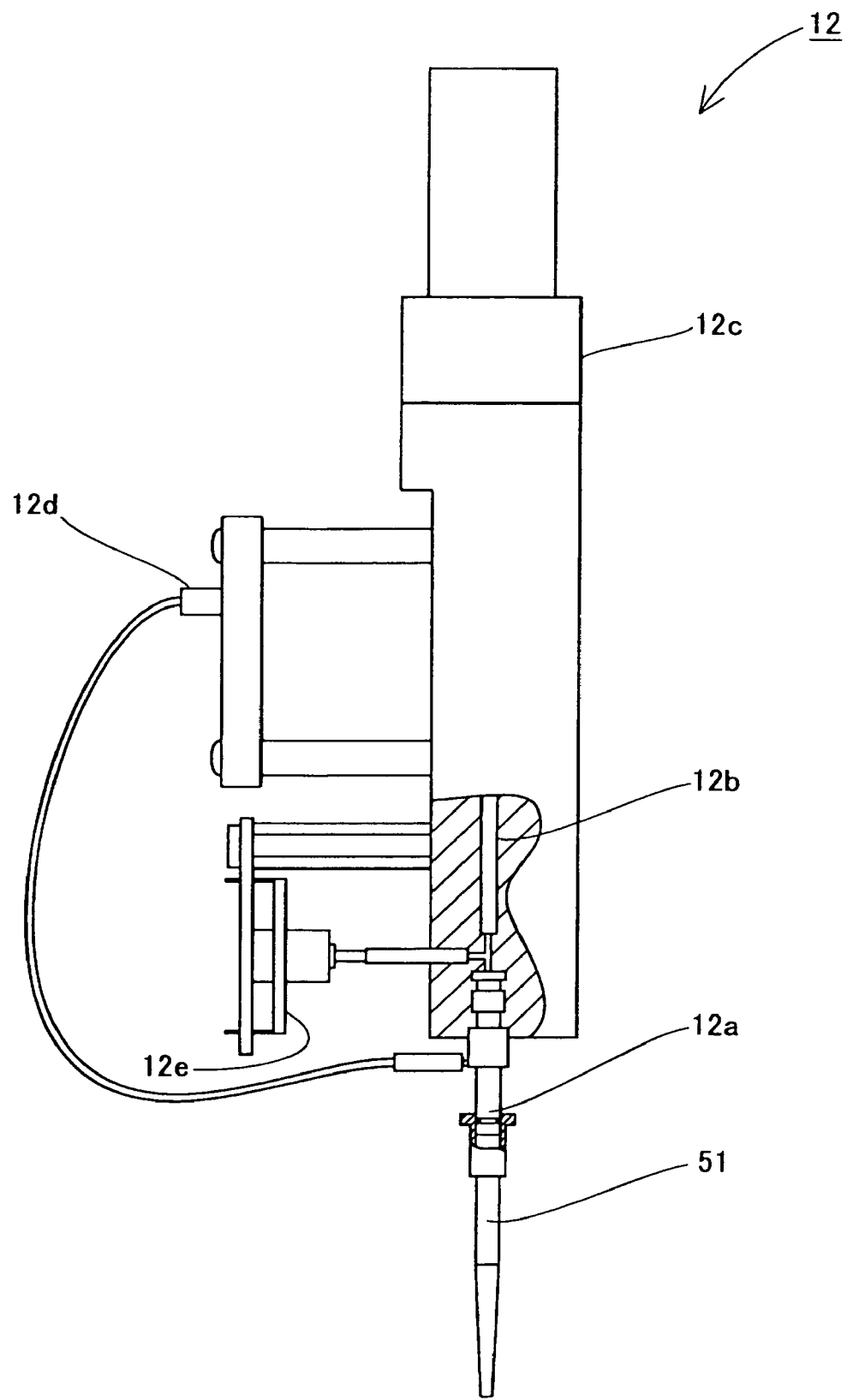
FIG. 5 is a schematic view showing the structure of a syringe portion in the measuring portion of the analyzing apparatus according to the embodiment illustrated in FIG. 2.
Figure 6:
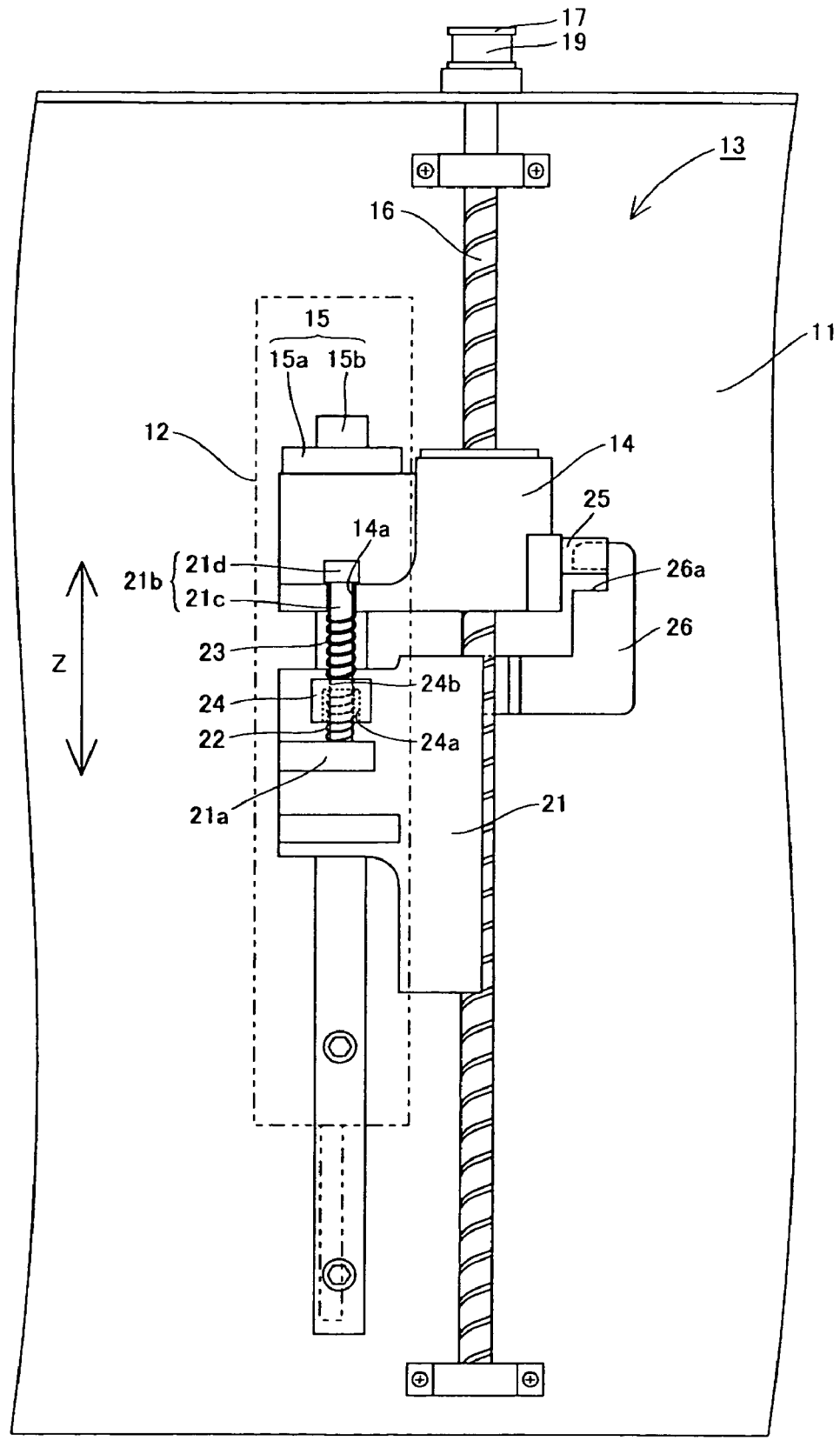
FIG. 6 is a schematic view showing the structure of the syringe up-down portion of the analyzing apparatus according to the embodiment illustrated in FIG. 2.
Figure 7:
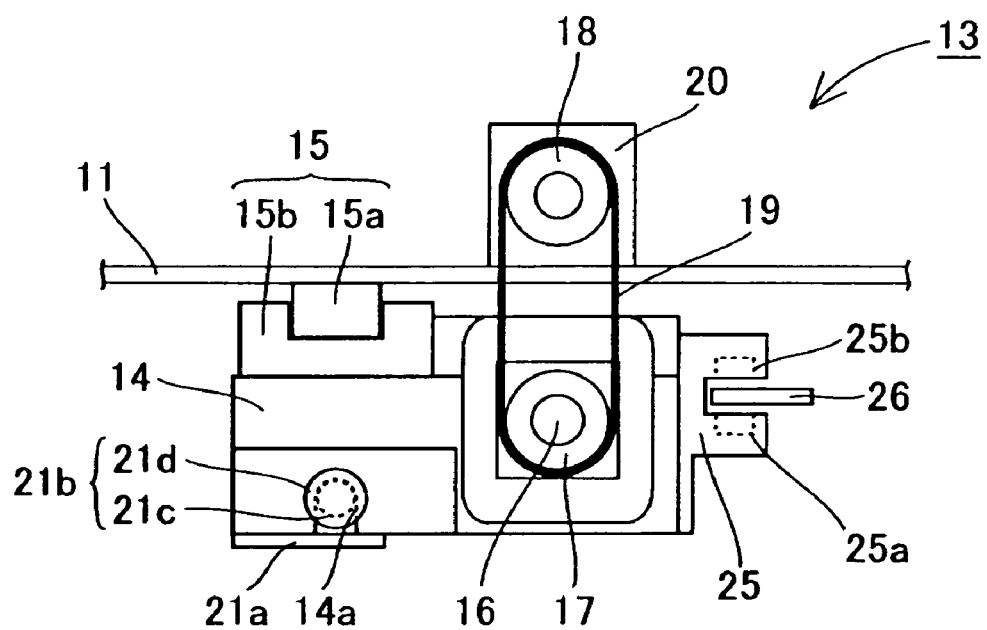
FIG. 7 is a schematic top view showing the syringe up-down portion according to the embodiment illustrated in FIG. 5.
Figure 8:
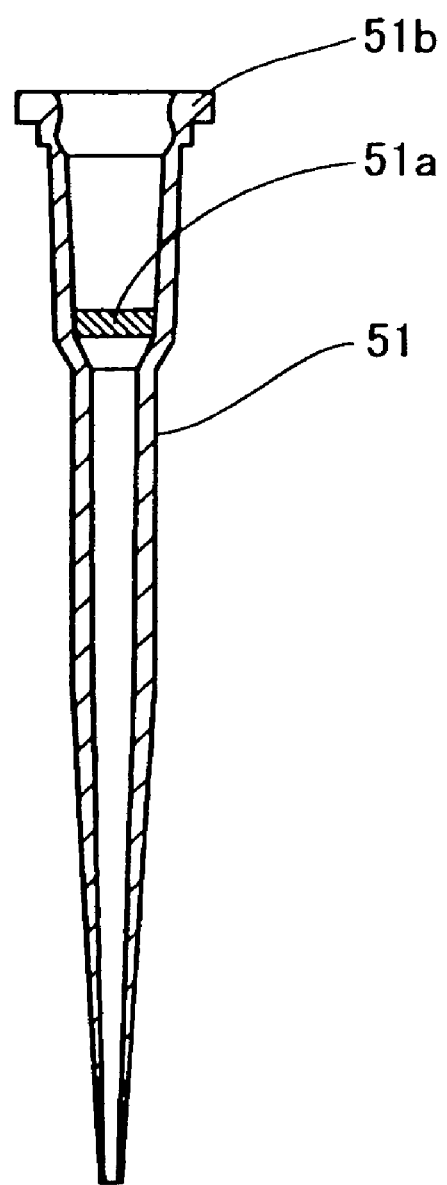
FIG. 8 is a sectional view showing the structure of a pipette chip to be used in the analyzing apparatus according to the embodiment illustrated in FIG. 2.
Figure 9:
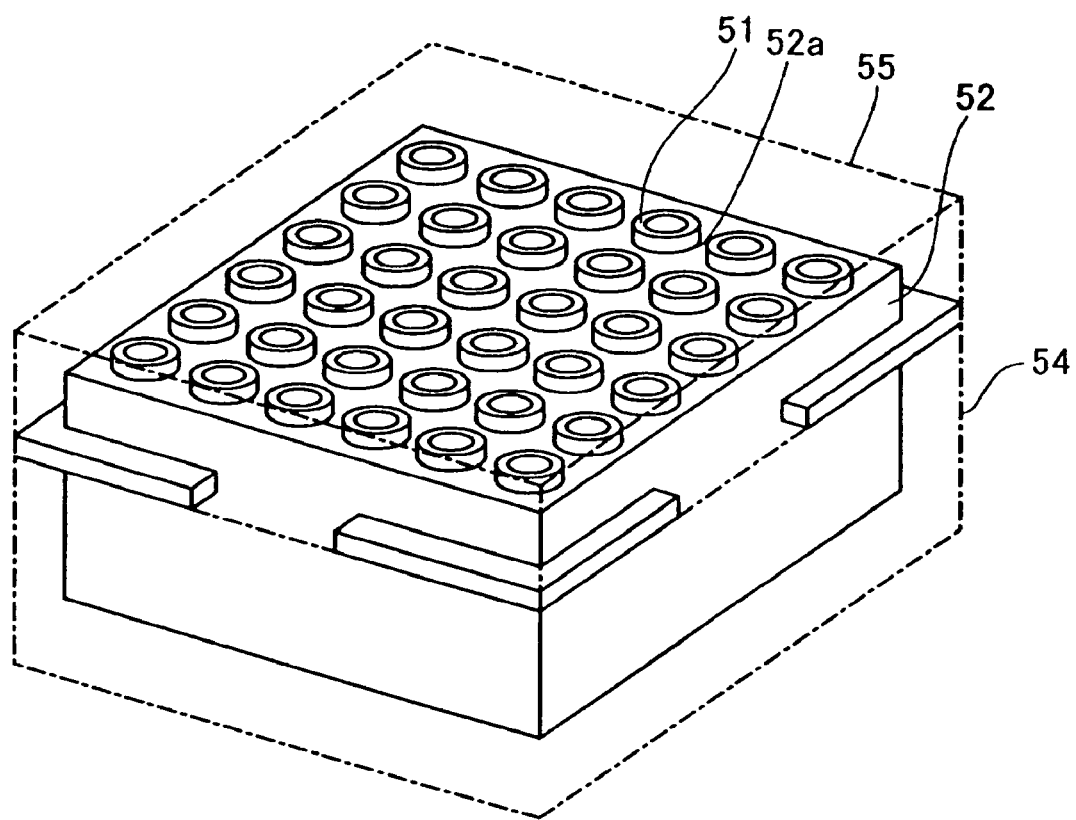
FIG. 9 is a perspective view showing the storage state of a rack for accommodating the pipette chip to be used in the analyzing apparatus according to the embodiment illustrated in FIG. 2.

FIG. 1 is a perspective view showing the whole structure of an analyzing apparatus and a data processing portion thereof according to an embodiment of the present invention. FIG. 2 is a perspective view showing the whole structure of the measuring portion of the analyzing apparatus illustrated in FIG. 1, and FIG. 3 is a schematic plan view of FIG. 2. FIG. 4 is a block diagram showing the structure of a controller illustrated in FIG. 2, FIG. 5 is a view showing the syringe portion of the measuring portion of the analyzing apparatus illustrated in FIG. 2, FIG. 6 is a schematic view showing the syringe up-down portion of the measuring portion of the analyzing apparatus illustrated in FIG. 2, and FIG. 7 is a schematic top view showing the syringe up-down portion in FIG. 6. FIGS. 8 and 9 are views showing a pipette chip and a rack in the measuring portion of the analyzing apparatus illustrated in FIG. 2. In the present embodiment, description will be given to a gene amplification detecting apparatus as an example of the analyzing apparatus including a dispensing device according to the present invention. The gene amplification detecting apparatus according to the present embodiment is an analyzing apparatus for supporting the cancer metastasis diagnosis of an excised tissue in a cancer operation and serves to amplify a gene (mRNA) caused by a cancer present in the excised tissue by using a LAMP (Loop-mediated Isothermal Amplification) method and to measure the turbidity of a solution generated with the amplification, thereby carrying out a detection. The details of the LAMP method have been disclosed in U.S. Pat. No. 6,410,278.

First of all, referring to FIG. 1, description will be given to the whole structure of the analyzing apparatus (the gene amplification detecting apparatus) and the data processing portion thereof according to the present embodiment. As shown in FIG. 1, an analyzing apparatus (a gene amplification detecting apparatus) 110 according to the present embodiment is constituted by a measuring portion 111 and a data processing portion 112 connected to the measuring portion 111 through a communication circuit. The data processing portion 112 is constituted by a personal computer including a keyboard 112a, a mouse 112b and a display portion 112c.

As shown in FIGS. 2 and 3, the measuring portion 111 includes a dispensing mechanism portion 10, a sample vessel set portion 30, a reagent vessel set portion 40, a chip set portion 50, a chip discarding portion 60, a reaction detecting portion 70 formed by five reaction detecting blocks 70a, and a transfer portion 80 for transferring the dispensing mechanism portion 10 in an XY-axis direction. Moreover, the measuring portion 111 includes a controller 90 and a power supply portion 100 for supplying a power to the whole apparatus including the controller 90 as shown in FIG. 2. Moreover, an emergency stop switch 101 is provided in the predetermined part of the front face of the measuring portion 111. As shown in FIG. 4, the controller 90 includes a CPU 91, a ROM 92, a RAM 93 and an input/output interface 94. The ROM 92 stores an operating system, a control program for controlling the operation of the apparatus, and necessary data for executing the control program. The CPU 91 can execute the control program with loading to the RAM 93 or directly from the ROM 92. Thus, data on the result of the processing of the CPU 91 are transmitted to each portion of the apparatus or the outside of the apparatus through the input/output interface 94, and the necessary data for the processing of the CPU 91 are received from each portion of the apparatus or the outside of the apparatus through the input/output interface 94.

Moreover, the dispensing mechanism portion 10 includes an arm portion 11 to be moved in the X-axis and Y-axis directions (a plane direction) by means of the transfer portion 80, two syringe portions 12 which can be moved in a Z-axis direction (a perpendicular direction) independently with respect to the arm portion 11 respectively and are arranged in a transverse direction, and a syringe up-down portion 13 for moving the syringe portion 12 in the Z-axis direction. Furthermore, the syringe portion 12 further includes a nozzle 12a to/from which a pipette chip 51 to be described below is attached/removed at a tip, a pump 12b for carrying out a suction and a discharge through the nozzle 12a, a motor 12c for driving the pump 12b, an electrostatic capacity sensor 12d, and a pressure detecting sensor 12e as shown in FIG. 5. In the pump 12b, moreover, it is possible to obtain the sucking and discharging functions of the syringe portion 12 by converting the rotation of the motor 12c into a piston motion. The electrostatic capacity sensor 12d is a sensor of an electrostatic capacity type and serves to detect the electrostatic capacities of the pipette chip 51 formed of a conductive resin and a liquid. In addition, the pressure detecting sensor 12e serves to detect a pressure in the suction and discharge to be carried out by the pump 12b. By the electrostatic capacity sensor 12d and the pressure detecting sensor 12e, whether the suction and discharge is surely carried out is detected.

As shown in FIGS. 6 and 7, furthermore, the syringe portion 13 is constituted by a base 14, a linear motion guide 15, a ball screw 16, a pulley 17 on a ball screw side, a pulley 18 on a motor side, a driving belt 19, a stepping motor 20, a syringe support portion 21, a lower compression coiled spring 22, an upper compression coiled spring 23, a stopper 24, a light transmission type sensor 25, and a shielding plate 26.

As shown in FIG. 7, moreover, the base 14 is attached to the front face of the arm portion 11 through a rail 15a and a slider 15b which constitute the linear motion guide 15. As shown in FIG. 6, moreover, the base 14 is engaged with the ball screw 16. The ball screw 16 is provided to be extended in the Z-axis direction (vertical direction). Furthermore, the pulley 17 on the ball screw side is attached to the upper end of the ball screw 16 as shown in FIGS. 6 and 7. In addition, the stepping motor 20 is provided on the back face of the arm portion 11, and furthermore, the pulley 18 on the motor side is attached to the shaft of the stepping motor 20. The driving belt 19 is attached between the pulley 17 on the ball screw side and the pulley 18 on the motor side. Consequently, the base 14 is constituted to be moved in the Z-axis direction (the vertical direction) along the rail 15a with the rotation of the ball screw 16 by the driving operation of the stepping motor 20.

Moreover, the syringe support portion 21 is provided below the base 14 and supports the syringe portion 12 as shown in FIG. 6. The syringe support portion 21 is fixed to a slider (not shown) attached slidably to the rail 15a in the same manner as the base 14. Consequently, the syringe support portion 21 is constituted movably in the Z-axis direction (the vertical direction) along the rail 15a. In the case in which the syringe support portion 21 is moved, the syringe portion 12 is also moved integrally with the syringe support portion 21. Furthermore, a regulating portion 21a is provided to be protruded from the front face of the syringe support portion 21. A support shaft 21b extended upward is provided integrally with the upper face of the regulating portion 21a. The support shaft 21b includes a cylindrical spring support portion 21c having a predetermined diameter and a cylindrical slip stopping portion 21d provided on the upper side of the spring support portion 21c and having a larger diameter than the diameter of the spring support portion 21c. As shown in FIG. 7, moreover, the base 14 is provided with a U-shaped nick portion 14a seen from above. The spring support portion 21c of the support shaft 21b is engaged with the nick portion 14a movably in the Z-axis direction and is constituted in such a manner that the support shaft 21b can be prevented from slipping from the nick portion 14a downward by the slip stopping portion 21d.

In the present embodiment, as shown in FIG. 6, the lower compression coiled spring 22, the upper compression coiled spring 23 and the stopper 24 are attached to the spring support portion 21c of the support shaft 21b, and the lower compression coiled spring 22 and the upper compression coiled spring 23 are provided in series through the stopper 24. Moreover, a spring constant k1 of the lower compression coiled spring 22 is set to have a smaller value than the value of a spring constant k2 of the upper compression coiled spring 23. Furthermore, the upper end of the upper compression coiled spring 23 abuts on the lower face of the base 14, and furthermore, the lower end of the lower compression coiled spring 22 abuts on the upper face of the regulating portion 21a of the syringe support portion 21. By the lower compression coiled spring 22 and the upper compression coiled spring 23, the syringe support portion 21 is energized in a separating direction from the base 14 (a downward direction). Consequently, the syringe support portion 21 is prevented from being moved in an approaching direction (an upward direction) with respect to the base 14.

In addition, the stopper 24 is provided with a concave portion 24a and a through hole 24b is formed on the bottom face of the concave portion 24a. Moreover, the stopper 24 is provided in such a manner that the opening portion side of the concave portion 24a is set to be a lower side, and the spring support portion 21c of the support shaft 21b is inserted in the through hole 24b. Furthermore, the stopper 24 is constituted to be relatively movable in the vertical direction with respect to the spring support portion 21c of the support shaft 21b. Furthermore, a part of the lower compression coiled spring 22 is accommodated in the concave portion 24a of the stopper 24. In addition, the lower compression coiled spring 22 is provided between the bottom face of the concave portion 24a of the stopper 24 and the upper face of the regulating portion 21a of the syringe support portion 21. Consequently, the lower end of the stopper 24 abuts on the upper face of the regulating portion 21a when the lower compression coiled spring 22 contracts, and the range of the contraction of the lower compression coiled spring 22 is thus regulated. More specifically, if the lower end of the stopper 24 abuts on the upper face of the regulating portion 21a when the lower compression coiled spring 22 contracts, the lower compression coiled spring 22 does not contract any more.

Moreover, the light transmission type sensor 25 is provided for detecting that the syringe portion 12 and the syringe support portion 21 are moved with respect to the base 14. The sensor 25 is attached to the side face of the base 14. Furthermore, the sensor 25 includes a light source portion 25a for irradiating a light and a light receiving portion 25b provided opposite to the light source portion 25a and serving to receive the light irradiated from the light source portion 25a as shown in FIG. 7. In addition, the sensor 25 is constituted to output an ON signal when the light receiving portion 25b receives a light irradiated from the light source portion 25a and to output an OFF signal when the light receiving portion 25b does not receive the light irradiated from the light source portion 25a. Moreover, the shielding plate 26 is provided to shield the light irradiated from the light source portion 25a of the sensor 25. The shielding plate 26 is attached to the syringe support portion 21 as shown in FIG. 6. Furthermore, the shielding plate 26 has a rectangular nick portion 26a. A portion including the nick portion 26a of the shielding plate 26 is provided between the light source portion 25a and the light receiving portion 25b in the sensor 25 as shown in FIG. 7. In addition, the nick portion 26a is provided in such a manner that the light irradiated from the light source portion 25a of the sensor 25 is incident on the light receiving portion 25b through the nick portion 26a when the syringe support portion 21 is moved in an upward direction so that the lower end of the stopper 24 abuts on the upper face of the regulating portion 21a of the syringe support portion 21.

Furthermore, the controller 90 serves to detect positions in the Z-axis direction (the vertical direction) of the syringe support portion 21 and the syringe portion 12 based on the number of driving pulses (the amount of driving) of the stepping motor 20. Moreover, the controller 90 is constituted to detect whether the nozzle 12a of the syringe portion 12 is normally attached to the pipette chip 51 based on the output signal (ON/OFF signal) of the sensor 25 and the amount of driving of the stepping motor 20 (the number of driving pulses).

As shown in FIGS. 2 and 3, moreover, a sample vessel set table 31 having five sample vessel set holes 31a and a holding portion 31b is removably fitted in a concave portion (not shown) of the sample vessel set portion 30. A sample vessel 32 accommodating a soluble extracted solution (sample) prepared by pretreating (homogenizing, filtering and diluting) an excised tissue is set to the five sample vessel set holes 31a of the sample vessel set table 31.

Furthermore, a reagent vessel set table 41 having two primer reagent vessel set holes 41a and one enzyme reagent vessel set hole 41b, and a holding portion 41c is removably fitted in a concave portion (not shown) of the reagent vessel set portion 40. The primer reagent vessel set hole 41a of the reagent vessel set table 41 is provided at a predetermined interval in the Y-axis direction, and the enzyme reagent vessel set hole 41b is provided on only the left side of a front face. A primer reagent vessel 42a accommodating the primer reagent of β-actin and an enzyme reagent vessel 42b accommodating a common enzyme reagent to cytokeratin (CK19) and the β-actin are provided in the primer reagent vessel set hole 41a and the enzyme reagent vessel set hole 41b which are provided on the left side of the front face (see FIG. 3), respectively. In addition, a primer reagent vessel 42a accommodating a CK19 primer reagent is provided in the primer reagent vessel set hole 41a provided on the right side of the front face.

Moreover, two racks 52 are removably fitted in two concave portions (not shown) of the chip set portion 50. Each of the racks 52 has housing holes 52a capable of accommodating 36 pipette chips 51. In addition, two removal buttons 53 are provided on the chip set portion 50. By pressing the removal button 53, it is possible to bring a state in which the rack 52 can be removed. The pipette chip 51 is formed by a conductive resin material containing carbon, and furthermore, a filter 51a is attached to an inner part as shown in FIG. 8. The filter 51a has a function of preventing an erroneous flow into the pump 12b for a liquid. An electron beam irradiation is carried out in a packing state before shipment in such a manner that a degradative enzyme such as human saliva which might be stuck in a process for manufacturing the pipette chip 51 does not adversely influence the amplification of a gene. Moreover, the rack 52 accommodating the pipette chip 51 is stored in a state in which a lower cover 54 and an upper cover 55 are attached as shown in FIG. 9 before setting to the chip set portion 50.

As shown in FIG. 3, furthermore, a chip discarding portion 60 is provided with two chip discarding holes 60a for discarding the used pipette chip 51. In addition, a trench portion 60b having a smaller width than that of the chip discarding hole 60a is provided continuously with the chip discarding hole 60a.

Moreover, each reaction detecting block 70a of a reaction detecting portion 70 is constituted by a reacting portion 71, two turbidity detecting portions 72, and a cover closing mechanism portion 73 as shown in FIG. 2. As shown in FIG. 3, each reacting portion 71 is provided with two detecting cell set holes 71a for setting a detecting cell 75.

As shown in FIG. 3, moreover, the turbidity detecting portion 72 is constituted by an LED light source portion 72a formed by a blue LED having a wavelength of 465 nm which is attached to a substrate 74a provided on one of the side faces of the reacting portion 71, and a photodiode light receiving portion 72b attached to the substrate 74b which is provided on the other side face of the reacting portion 71.

Each reaction detecting block 70a is provided with two sets of turbidity detecting portions 72, each of which is constituted by an LED light source portion 72a and a photodiode light receiving portion 72b. Accordingly, five reaction detecting blocks 70a are provided with ten sets of turbidity detecting portions 72 including the LED light source portions 72a and the photodiode light receiving portions 72b in total. The LED light source portion 72a and the photodiode light receiving portion 72b corresponding thereto are provided in such a manner that a light having a diameter of approximately 1 mm is irradiated from the LED light source portion 72a onto the lower part of the detecting cell 75 and a light can be thus received by the photodiode light receiving portion 72b. The LED light source portion 72a and the photodiode light receiving portion 72b have a function of detecting the presence of the detecting cell 75 depending on the intensity of a light received by the photodiode light receiving portion 72b and detecting (monitoring) the turbidity of a solution accommodated in the detecting cell 75 in real time.

As shown in FIGS. 2 and 3, moreover, the transfer portion 80 includes a linear motion guide 81 and a ball screw 82 for transferring the dispensing mechanism portion 10 in the Y-axis direction, a stepping motor 83 for driving the ball screw 82, a linear motion guide 84 and a ball screw 85 for transferring the dispensing mechanism portion 10 in the X-axis direction, and a stepping motor 86 for driving the ball screw 85. As shown in FIG. 3, furthermore, a rail portion 81a of the linear motion guide 81 and a support portion 82a of the ball screw 82 in the Y-axis direction are attached to a frame 87. In addition, the other support portion 82b of the ball screw 82 is attached to the frame 87 through the stepping motor 83. Moreover, a slide portion 81b of the linear motion guide 81 in the Y-axis direction and a straight moving portion (not shown) of the ball screw 82 are attached to the arm portion 11 of the dispensing mechanism portion 10. Furthermore, a rail portion 84a of the linear motion guide 84 in the X-axis direction and a support portion 85a of the ball screw 85 are attached to a support table 88. In addition, a slide portion (not shown) of the linear motion guide 84 in the X-axis direction and the other support portion 85b of the ball screw 85 are attached to the frame 87. Moreover, a stepping motor 86 is attached to the other support portion 85b of the ball screw 85. A transfer in the XY-axis direction of the dispensing mechanism portion 10 is carried out by rotating the ball screws 82 and 85 through the stepping motors 83 and 86, respectively.

FIGS. 10 to 15 are views for explaining the operation of the analyzing apparatus according to an embodiment of the present invention. A "first state", a "second state" and a "third state" in FIG. 11 correspond to the states of the base and the syringe support portion in FIGS. 6, 12 and 13, respectively. Referring to FIGS. 1 to 15, next, description will be given to the operation of the analyzing apparatus (gene amplification detecting apparatus) according to the present embodiment. In the gene amplification detecting apparatus according to the present embodiment, as described above, a gene (mRNA) caused by a cancer present in an excised tissue in a cancer operation is amplified by using a LAMP method and the turbidity of a solution generated with the amplification is measured to carry out a detection.

First of all, as shown in FIGS. 2 and 3, the sample vessel 32 accommodating a soluble extracted solution (sample) prepared by pretreating (homogenizing, filtering and diluting) an excised tissue is set to the sample vessel set hole 31a of the sample vessel set table 31. Moreover, the primer reagent vessel 42a accommodating the primer reagent of the β-actin and the enzyme reagent vessel 42b accommodating a common enzyme reagent to the cytokeratin (CK19) and the β-actin are set to the primer reagent vessel set hole 41a and the enzyme reagent vessel set hole 41b which are provided on the left side of the front face, respectively. Furthermore, the primer reagent vessel 42a accommodating the primer reagent of the CK19 is set to the primer reagent vessel set hole 41a provided on the right side of the front face. In addition, each of the two racks 52 which accommodates 36 disposable pipette chips 51 is fitted in the concave portion (not shown) of the chip set portion 50. In this case, the initial position (origin position) of the arm portion 11 of the dispensing mechanism portion 10 is shifted from the upper part of the chip set portion 50 as shown in FIGS. 2 and 3. Therefore, the two racks 52 can easily be fitted in the concave portion (not shown) of the chip set portion 50. Furthermore, two cell portions 76a of the detecting cell 75 are set to two detecting cell set holes 71a of the reacting portion 71 of each reaction detecting block 70a.

After a measuring item and a sample registration are executed by using the keyboard 112a and the mouse 112b of the data processing portion 112 shown in FIG. 1, the operation of the measuring portion 111 is started by means of the keyboard 112a or the mouse 112b.

When the operation of the measuring portion 111 is started, the arm portion 11 of the dispensing mechanism portion 10 is first moved from the initial position to the chip set portion 50 by means of the transfer portion 80. Then, the stepping motor 20 of the syringe up-down portion 13 (see FIG. 7) is driven so that the ball screw 16 is rotated. Consequently, the base 14 of the syringe up-down portion 13 is moved in a downward direction. In the chip set portion 50 (see FIG. 2), consequently, the two syringe portions 12 of the dispensing mechanism portion 10 and the syringe support portion 21 are moved in the downward direction.

Figure 10:
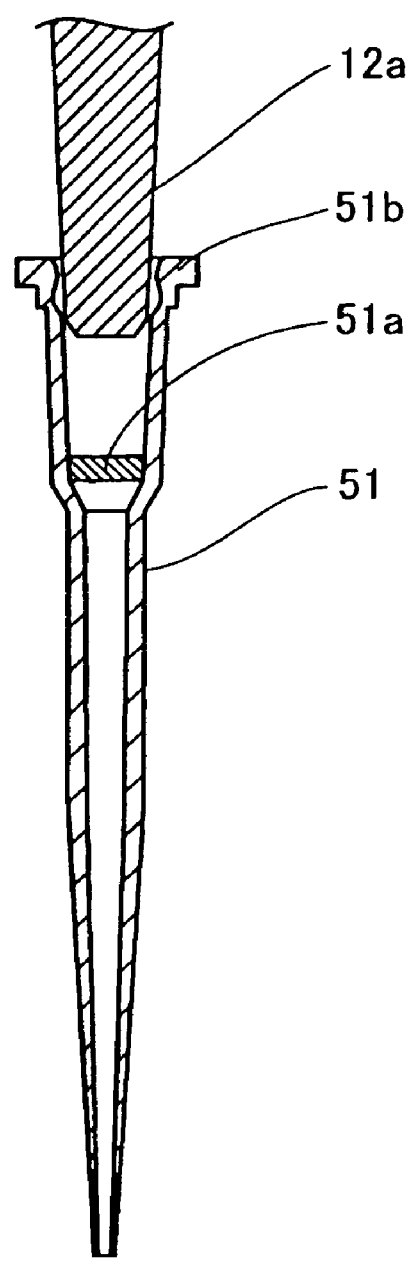
FIG. 10 is a sectional view showing a state in which the nozzle of the syringe portion of the analyzing apparatus according to the embodiment illustrated in FIG. 2 is normally inserted in the pipette chip.
Figure 11:
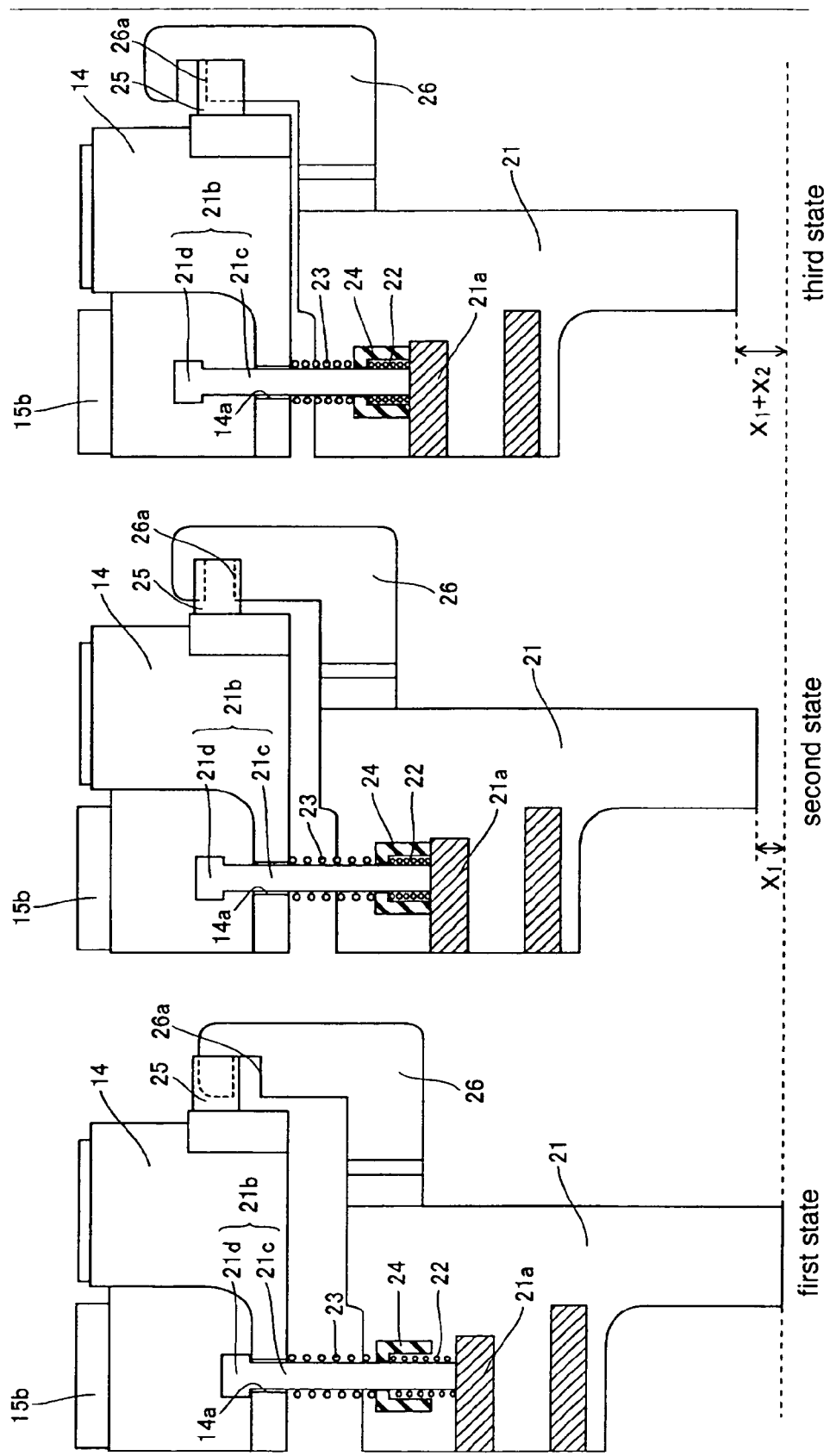
FIG. 11 is a view for explaining the operation of the analyzing apparatus according to the embodiment of the present invention.
Figure 12:
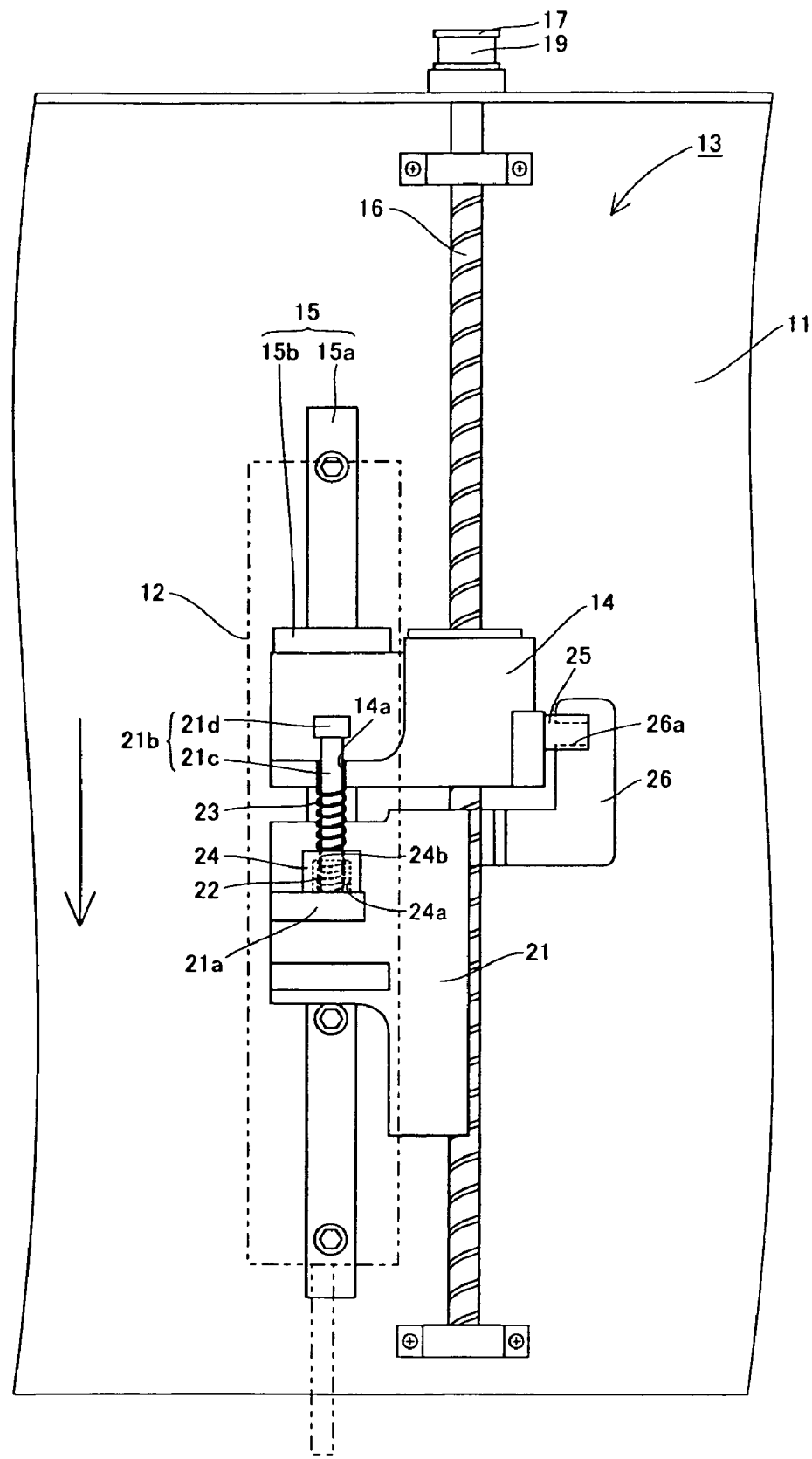
FIG. 12 is a view for explaining the operation of the analyzing apparatus according to the embodiment of the present invention.

In this case, in the present embodiment, in the case in which the tip of the nozzle 12a of the syringe portion 12 is normally inserted in the opening portion of the upper part of the pipette chip 51 as shown in FIG. 10, the nozzle 12a abuts on the internal wall surface of the pipette chip 51 when the tip of the nozzle 12a reaches a downward position from the upper face of a flange portion 51b of the pipette chip 51 by approximately 2 mm to 3 mm. Consequently, the nozzle 12a receives an upward force. Therefore, the syringe portion 12 and the syringe support portion 21 are moved in an upward direction by a distance x1 (see FIG. 11) with respect to the base 14 while causing the lower compression coiled spring 22 to contract. Thus, the syringe portion 12 and the syringe support portion 21 are changed from a first state (see FIGS. 6 and 11) in which the nozzle 12a does not abut on the pipette chip 51 to a second state (see FIGS. 11 and 12). In this case, as shown in FIG. 11, the lower compression coiled spring 22 contracts by the distance x1 so that the lower end of the stopper 24 abuts on the upper face of the regulating portion 21a of the syringe support portion 21. Consequently, the lower compression coiled spring 22 contracts by the distance x1 or less. In this case, moreover, the syringe support portion 21 and the syringe portion 12 are energized in a downward direction by an elastic force of $F1=k1 \times x1$ by means of the lower compression coiled spring 22.

In the first state described above, as shown in FIG. 11, a portion between the light source portion 25a (see FIG. 7) and the light receiving portion 25b (see FIG. 7) in the sensor 25 is blocked through an upper part from the nick portion 26a of the shielding plate 26 attached to the syringe support portion 21. Consequently, the sensor 25 is brought into an OFF state. When the change to the second state is carried out, a light is incident from the light source portion 25a (see FIG. 7) of the sensor 25 to the light receiving portion 25b (see FIG. 7) through the nick portion 26a of the shielding plate 26 so that the sensor 25 is brought into an ON state. In this case, the controller 90 decides whether or not the output of the sensor 25 is set into the ON state when the nozzle 12a of the syringe portion 12 reaches a preset normal downward position based on the number of the driving pulses of the stepping motor 20 and the output of the sensor 25. If the controller 90 decides that the sensor 25 is set into the ON state when the nozzle 12a of the syringe portion 12 reaches the preset normal downward position (see FIG. 10), it is decided that the nozzle 12a of the syringe portion 12 is brought down to a position in which it is normally pressed into the pipette chip 51.

Figure 15:
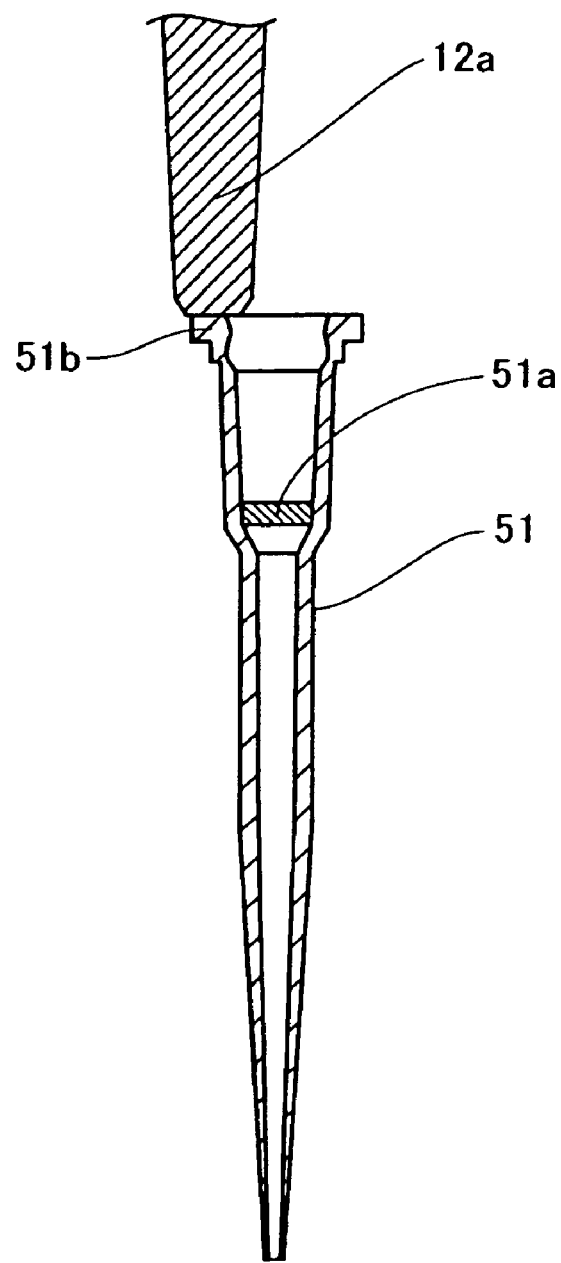
FIG. 15 is a sectional view showing a state in which the nozzle of the syringe portion of the analyzing apparatus according to the embodiment illustrated in FIG. 2 is provided in contact with the pipette chip.

On the other hand, as shown in FIG. 15, also in the case in which the tip of the nozzle 12a comes in contact with the flange portion 51b of the pipette chip 51 when the syringe potion 12 is moved in a downward direction, the nozzle 12a receives a force in an upward direction. Therefore, the syringe portion 12 and the syringe support portion 21 are changed from the first state (see FIGS. 6 and 11) to the second state (see FIGS. 11 and 12). In this case, the controller 90 decides that the sensor 25 is set into the ON state before the nozzle 12a of the syringe portion 12 reaches the preset normal downward position based on the number of the driving pulses of the stepping motor 20 and the output of the sensor 25, and furthermore, decides that the nozzle 12a of the syringe portion 12 comes in contact with the flange portion 51b of the pipette chip 51. Thus, there is detected the contact of the nozzle 12a in the movement of the syringe portion 12 in the downward direction. The spring constant k1 of the lower compression coiled spring 22 is much smaller than the spring constant k2 of the upper compression coiled spring 23. Also in the case in which the nozzle 12a comes in contact with the pipette chip 51 by a very small force, therefore, the contact can easily be detected. In the case in which the contact of the nozzle 12a is detected, moreover, the controller 90 stops the movement of the base 14 in the downward direction and then causes the display portion 112c of the data processing portion 112 to display an error message. Thereafter an error return processing is carried out by a user.

Figure 13:
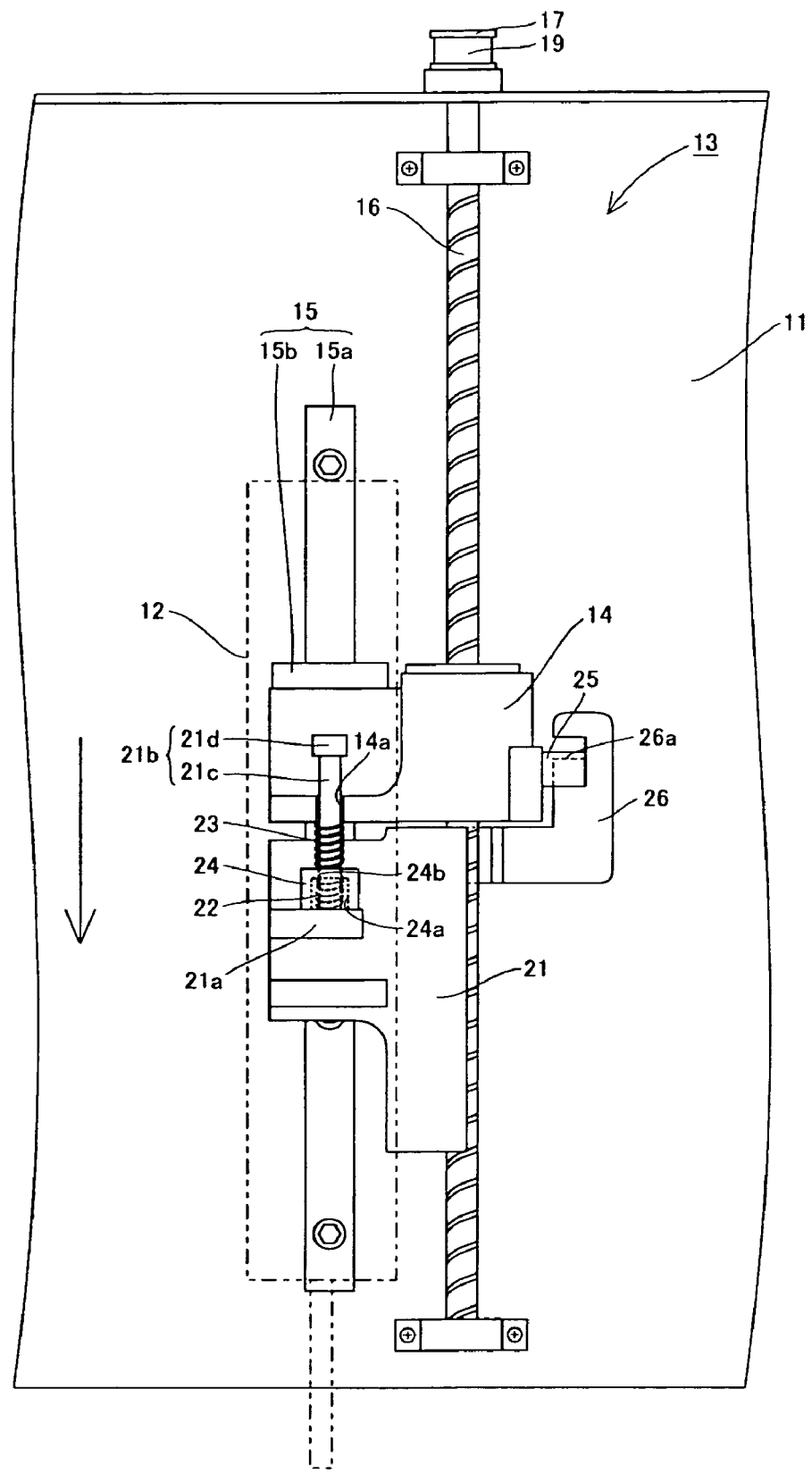
FIG. 13 is a view for explaining the operation of the analyzing apparatus according to the embodiment of the present invention.
Figure 14:
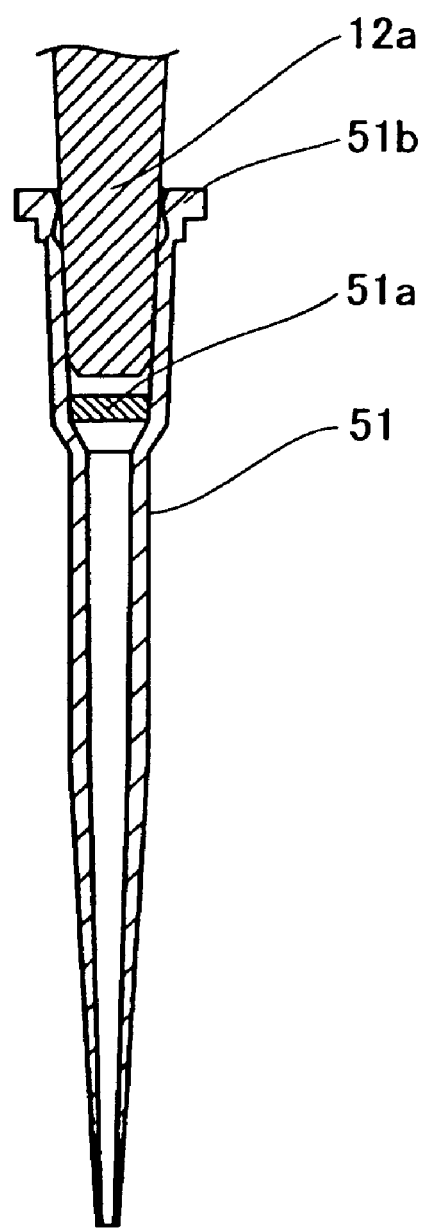
FIG. 14 is a sectional view showing a state in which the nozzle of the syringe portion of the analyzing apparatus according to the embodiment illustrated in FIG. 2 is normally pressed into the pipette chip.

In the second state described above, in the case in which the controller 90 decides that the nozzle 12a is brought down to the position in which it is normally pressed into the pipette chip 51, the base 14, the syringe support portion 21 and the syringe portion 12 are moved by a distance x2 (see FIG. 11) in a further downward direction from the second state. Consequently, the syringe support portion 21 and the syringe portion 12 are moved in the upward direction by the distance x2 with respect to the base 14. As a result, a third state shown in FIGS. 11 and 13 is brought. In this case, the upper compression coiled spring 23 is caused to contract by the distance x2. Therefore, the syringe support portion 21 and the syringe portion 12 are energized in the downward direction by an elastic force of $F2=k1 \times x1+k2 \times x2$ by means of the lower compression coiled spring 22 and the upper compression coiled spring 23. In this case, the spring constant k2 of the upper compression coiled spring 23 is greater than the spring constant of the lower compression coiled spring. Therefore, the elastic force F2 generated by the lower compression coiled spring and the upper compression coiled spring becomes comparatively great. In the third state, consequently, the nozzle 12a of the syringe portion 12 is pressed into the opening portion of the upper part of the pipette chip 51 by the elastic force F2. As shown in FIG. 14, the nozzle 12a is pressed into a position in which a distance from the tip of the nozzle 12a to the filter 51a of the pipette chip 51 is approximately 1 mm. In this case, as shown in FIGS. 11 and 13, a portion between the light source portion 25a (see FIG. 7) and the light receiving portion 25b (see FIG. 7) in the sensor 25 is blocked by a lower part from the nick portion 26a of the shielding plate 26. Therefore, the sensor 25 is brought into the OFF state.

In the case in which the tip of the nozzle 12a of the syringe portion 12 is normally pressed into the opening portion of the upper part of the pipette chip 51, the pipette chip 51 is attached to the tip of the nozzle 12a in each of the two syringe portions 12 as shown in FIG. 5. After the two syringe portions 12 are moved upward by the operation of the stepping motor 20, the arm portion 11 of the dispensing mechanism portion 10 is moved in the X-axis direction toward the upper parts of the two primer reagent vessels 42a accommodating the primer reagents of the CK19 and the β-actin which are set onto the reagent vessel set table 41 by means of the transfer portion 80. Then, the stepping motor 20 is driven so that the two syringe portions 12 are moved in the downward direction. Consequently, the tips of the two pipette chips 51 attached to the nozzles 12a of the two syringe portions 12 are inserted into the liquid levels of the primer reagents of the CK19 and the β-actin in the two primer reagent vessels 42a, respectively. Thereafter, the primer reagents of the CK19 and the β-actin in the two primer reagent vessels 42a are sucked by the pump 12b of the syringe portion 12.

When the primer reagent is sucked, it is detected, by the electrostatic capacity sensor 12d (see FIG. 5), that the tip of the pipette chip 51 formed by a conductive resin comes in contact with the liquid level, and a pressure in the suction of the pump 12b is detected by the pressure detecting sensor 12e (see FIG. 5). Upon receipt of signals output from the electrostatic capacity sensor 12d and the pressure detecting sensor 12e, the controller 90 detects whether or not the suction is reliably carried out.

After the suction of the primer reagent, the stepping motor 20 is driven so that the two syringe portions 12 are moved upward and the arm portion 11 of the dispensing mechanism portion 10 is then moved toward the upper part of the reaction detecting block 70a positioned on an innermost side (the inner side of the front face of the apparatus) by means of the transfer portion 80. The two syringe portions 12 positioned in the upper part of the reaction detecting block 70a on the innermost side are moved in the downward direction by the operation of the stepping motor 20. Consequently, the two pipette chips 51 attached to the nozzles 12a of the two syringe portions 12 are inserted into the two cell portions 76a of the detecting cell 75, respectively. By using the pump 12b of the syringe portion 12, then, the two primer reagents of the CK19 and the β-actin are discharged to the two cell portions 76a, respectively. Also in case of the discharge (exhaust), in the same manner as in the case of the suction, it is detected that the tip of the pipette chip 41 formed by the conductive resin comes in contact with the liquid level by means of the electrostatic capacity sensor 12d (see FIG. 5) (liquid level detection), and furthermore, a pressure in the discharge of the pump 12b is detected by means of the pressure detecting sensor 12e. The signals output from the electrostatic capacity sensor 12d and the pressure detecting sensor 12e are given to the controller 90 so that the controller 90 detects whether or not the discharge is reliably carried out. Also in the suction and discharge of the following enzyme reagent and sample, a liquid level is detected by means of the electrostatic capacity sensor 12d and a pressure in a suction and discharge is detected by means of the pressure detecting sensor 12e in the same manner as described above.

After the primer reagent is discharged, the two syringe portions 12 are moved upward by the operation of the stepping motor 20. Then, the arm portion 11 of the dispensing mechanism portion 10 is moved in the X-axis direction toward the upper part of the chip discarding portion 60 by means of the transfer portion 80. Thereafter, the pipette chip 51 is discarded in the chip discarding portion 60. More specifically, the two syringe portions 12 are moved in the downward direction by the operation of the stepping motor 20 so that the pipette chip 51 is inserted into the two chip discarding holes 60a (see FIG. 3) of the chip discarding portion 60. In this state, the arm portion 11 of the dispensing mechanism portion 10 is moved in the Y-axis direction by means of the transfer portion 80. Consequently, the pipette chip 51 is moved to the lower part of the trench portion 60b. Then, the stepping motor 20 is driven so that the two syringe portions 12 are moved in the upward direction. Therefore, the collar portion of the upper face of the pipette chip 51 abuts on lower faces at both sides of the trench portion 60b and receives a force in the downward direction from the lower faces thereof. Consequently, the pipette chip 51 is automatically separated from the nozzles 12a of the two syringe portions 12. Thus, the pipette chip 51 is discarded into the chip discarding portion 60. While the pipette chip 51 discarded into the chip discarding portion 60 is exactly discarded in the present embodiment, it is not restricted thereto but the pipette chip 51 collected in the chip discarding portion 60 may be washed and recycled.

Next, the arm portion 11 of the dispensing mechanism portion 10 is moved to the chip set portion 50 by means of the transfer portion 80 again. After the syringe portion 12 is moved to the chip set portion 50, two new pipette chips 51 are automatically attached to the tips of the nozzles 12a of the two syringe portions 12 by the same operation as described above in the chip set portion 50. Thereafter, the arm portion 11 of the dispensing mechanism portion 10 is moved in the X-axis direction by means of the transfer portion 80 toward the upper part of the enzyme reagent vessel 42b accommodating a common enzyme reagent to the CK19 and the β-actin which is set to the reagent vessel set table 41, and the enzyme reagent in the enzyme reagent vessel 42b is then sucked. More specifically, first of all, the stepping motor 20 and the pump 12b are driven so that one of the syringe portions 12 positioned in the upper part of the enzyme reagent vessel 42b is moved in the downward direction to suck the enzyme reagent and the same syringe portion 12 is then moved in the upward direction. Thereafter, the arm portion 11 of the dispensing mechanism portion 10 is moved in the Y-axis direction by means of the transfer portion 80 in such a manner that the other syringe portion 12 is positioned above the same enzyme reagent vessel 42b. Subsequently, the stepping motor 20 and the pump 12b are driven so that the other syringe portion 12 is moved in the downward direction to suck the enzyme reagent from the same enzyme reagent vessel 42b, and then, the other syringe portion 12 is moved in the upward direction. After the arm portion 11 of the dispensing mechanism portion 10 is moved toward the upper part of the reaction detecting block 70a on an innermost side by means of the transfer portion 80, the common enzyme reagent to the CK19 and the β-actin is discharged to the two cell portions 76a of the detecting cell 75. After the enzyme reagent is discharged, the arm portion 11 of the dispensing mechanism portion 10 is moved toward the upper part of the chip discarding portion 60 by means of the transfer portion 80 and the pipette chip 51 is then discarded.

Next, the arm portion 11 of the dispensing mechanism portion 10 is moved to the chip set portion 50 by means of the transfer portion 80 again. Then, two new pipette chips 51 are automatically attached to the tips of the nozzles 12a of the two syringe portions 12 by the same operation as described above. Thereafter, the arm portion 11 of the dispensing mechanism portion 10 is moved in the X-axis direction toward the upper part of the sample vessel 32 accommodating a sample which is set to the sample vessel set table 31 by means of the transfer portion 80. By the same operation as the operation for sucking the enzyme reagent, thereafter, the sample in the sample vessel 32 is sucked. Subsequently, the arm portion 11 of the dispensing mechanism portion 10 is moved toward the upper part of the reaction detecting block 70a on the innermost side by means of the transfer portion 80. Then, the two syringe portions 12 are moved in the downward direction so that the same sample is discharged to the two cell portions 76a of the detecting cell 75.

When the sample is to be discharged to the two cell portions 76a of the detecting cell 75, the sucking and discharging operations are repeated at plural times by using the pumps 12b of the two syringe portions 12 so that the primer reagent and the enzyme reagent of the CK19 and the β-actin accommodated in the two cell portions 76a and the sample are stirred. In the dispensing of the primer reagent, the enzyme reagent and the sample, the temperature of a liquid in the detecting cell 75 is held at approximately 20° C. Then, the arm portion 11 of the dispensing mechanism portion 10 is moved toward the upper part of the chip discarding portion 60 by means of the transfer portion 80 and the pipette chip 51 is thereafter discarded.

After the primer reagent, the enzyme reagent and the sample are discharged into the cell portion 76a, the cover closing operation of the cover portion 77a of the detecting cell 75 is carried out. After the cover closing operation is completed, the temperature of the liquid in the detecting cell 75 is raised from approximately 20° C. to approximately 65° C., thereby amplifying a target gene (mRNA) by a LAMP (gene amplification) reaction. Then, a cloud generated by magnesium pyrophosphate prepared with the amplification is detected by a nephelometry. More specifically, a liquid turbidity in the detecting cell 75 in the amplifying reaction is detected (monitored) in real time by using the LED light source portion 72a and the photodiode light receiving portion 72b shown in FIG. 3, thereby detecting the liquid turbidity.

In the present embodiment, there is employed the structure in which the lower compression coiled spring 22 and the upper compression coiled spring 23 for suppressing the movement of the syringe portion 12 and the syringe support portion 21 with respect to the base 14 are provided and the lower compression coiled spring 22 has the smaller spring constant k1 than the spring constant k2 of the upper compression coiled spring 23 as described above. In the case in which the nozzle 12a of the syringe portion 12 comes in contact with the flange portion 51b of the pipette chip 51 by a very small force, consequently, the syringe support portion 21 is moved while causing the lower compression coiled spring 22 having the smaller spring constant k1 than the spring constant k2 of the upper compression coiled spring 23 to contract. Accordingly, it is possible to detect, by the sensor 25, that the syringe portion 12 is moved with respect to the base 14. Also in the case in which the nozzle 12a of the syringe portion 12 comes in contact with the pipette chip 51 by the very small force, therefore, the contact of the syringe portion 12 can be detected. Consequently, it is possible to enhance precision in the detection of the contact of the syringe portion 12. In the case in which the nozzle 12a of the syringe portion 12 is pressed into the pipette chip 51, moreover, a great cushion effect (shock absorbing effect) can be obtained by the elastic force of the upper compression coiled spring 23 having the greater spring constant k2 than the spring constant k1 of the lower compression coiled spring 22. Therefore, it is possible to sufficiently relieve a shock when pressing the nozzle 12a of the syringe portion 12 into the pipette chip 51. Consequently, it is possible to prevent the syringe portion 12 and the pipette chip 51 from being broken when pressing the nozzle 12a of the syringe portion 12 into the pipette chip 51.

The disclosed embodiment is illustrative in all respects and should not be construed to be restricted. The scope of the present invention is not described in the explanation of the embodiment but claims, and furthermore, equivalents to the claims and all changes therein are included.

For example, while there has been described the example in which the analyzing apparatus including the dispensing device according to the present invention is applied to the gene amplification detecting apparatus for amplifying a target gene by a LAMP method in the above embodiment, the present invention is not restricted thereto but the same analyzing apparatus may be applied to a gene amplification detecting apparatus for amplifying a target gene by a polymerase chain reaction method (PCR method) or a ligase chain reaction method (LCR method). Moreover, the analyzing apparatus including the dispensing device according to the present invention may be applied to an analyzing apparatus other than the gene amplification detecting apparatus. Moreover, it is also possible to singly use the dispensing device according to the present invention.

While the compression coiled spring is used as the elastic member in the above embodiment, moreover, the present invention is not restricted thereto but an elastic member other than the compression coiled spring, for example, rubber may be used. Furthermore, it is also possible to use means for generating an energizing force with respect to the movement of the syringe portion 12 other than the elastic member, for example, an energizing force generating mechanism for generating the energizing force by an actuator such as a motor or a cylinder. In addition, it is also possible to fix a holding member for holding the support shaft 21b to the base 14 and to cause a force in a downward direction to act on the syringe support portion 21 when the syringe support portion 21 is moved upward with respect to the base 14 by the holding force of the holding member. In this case, it is possible to change the holding force in the middle of the movement of the syringe support portion 21 to vary the magnitude of an effort for the syringe support portion 21, for example, thereby reducing the effort at the early stage of the movement to detect the contact of the syringe portion 12 with the pipette chip 51 with high precision and increasing the effort in the middle of the movement to sufficiently relieve a shock caused by the contact of the nozzle 12a with the pipette chip 51. In addition, it is possible to arrange two holding members over the moving path of the support shaft 21b, to support the support shaft 21b by only one of the holding members at the early stage of the movement of the syringe support portion 21, to apply a small effort to the syringe support portion 21 at this time, to insert the support shaft 21b into the other holding member by the movement of the syringe support portion 21, thereby supporting the support shaft 21b by both of the support members to apply a great effort to the syringe support portion 21, and furthermore, it is also possible to attenuate the upward movement of the syringe support portion 21 with respect to the base 14 by means of two kinds of dampers, thereby changing the attenuating force in the middle of the movement.

While the lower compression coiled spring 22 having a small elastic constant is provided on the underside of the upper compression coiled spring 23 having a great elastic constant in the above embodiment, moreover, it is not restricted thereto but the compression coiled spring having a great elastic constant may be provided on the underside of the compression coiled spring having a small elastic constant.

While the lower compression coiled spring 22 and the upper compression coiled spring 23 are provided in series in the above embodiment, furthermore, the present invention is not restricted thereto but the lower compression coiled spring 22 and the upper compression coiled spring 23 may be provided along separate axes, respectively. In addition, the diameters and lengths of the two compression coiled springs may be different from each other and one of the compression coiled springs may be provided to surround the outside of the other compression coiled spring. In this case, after the longer compression coiled spring contracts earlier and the lengths of both of the compression coiled springs become equal to each other, both of the compression coiled springs contract at the same time. Accordingly, an energizing force acting on the syringe portion 12 is small while only the longer compression coiled spring contracts. Therefore, the contact of the syringe portion 12 with the pipette chip 51 can be detected with high precision for the time. Moreover, the energizing force acting on the syringe portion 12 is great while both of the compression coiled springs contract. Therefore, it is possible to sufficiently relieve a shock caused by the contact of the nozzle 12a with the pipette chip 51 for the time.

Although the optical sensor is used as the detector in the above embodiment, furthermore, the present invention is not restricted thereto but an electrical sensor such as a microswitch may be used as the detector.

While the description has been given, as an example, to the case in which the present invention is applied when the chip attaching member is detected to come in contact with the dispensing chip in the above embodiment, furthermore, the present invention is not restricted thereto but the present invention can also be applied when the chip attaching member having the dispensing chip attached thereto is detected to come in contact with another predetermined object in a movement in a downward direction.

The foregoing detailed description and accompanying drawings have been provided by way of explanation and illustration, and are not intended to limit the scope of the appended claims. Many variations in the presently preferred embodiments illustrated herein will be obvious to one of ordinary skill in the art, and remain within the scope of the appended claims and their equivalents.

The invention claimed is:

1. A dispensing device comprising: a base which can be moved in a first direction; a chip attaching member which is provided movably in a second direction to be an opposite direction to the first direction with respect to the base and to which a dispensing chip is attached by a movement of the base in the first direction; first energizing means for giving a first energizing force directed in the first direction to the chip attaching member; second energizing means for giving a second energizing force directed at the first direction to the chip attaching member, the second energizing force being greater than the first energizing force; and a detector for detecting that the chip attaching member is moved at the second direction with respect to the base.

2. The dispensing device of claim 1, wherein the first energizing means comprises a first spring member having a first spring constant; and
the second energizing means comprises a second spring member having a greater second spring constant than the first spring constant.

3. The dispensing device of claim 1, wherein the chip attaching member comprises a nozzle to which the dispensing chip is attached, a syringe pump connected to the nozzle and for sucking and discharging a predetermined liquid through the dispensing chip and the nozzle, and a syringe driving source connected to the syringe pump and for driving the syringe pump.

4. The dispensing device of claim 1, further comprising:
a driving source for moving the base; and
a controller for monitoring whether or not the dispensing chip is normally attached to the chip attaching member based on an amount of driving of the driving source and an output of the detector.

5. A dispensing device comprising:
a base which can be moved in a first direction;
a chip attaching member which is provided movably by a predetermined moving range in a second direction opposite to the first direction with respect to the base, and to which a dispensing chip can be removably attached by a movement of the base in the first direction;
effort applying means for applying an effort to the chip attaching member in the first direction and changing a magnitude of the effort when the chip attaching member moved in the second direction with respect to the base; and
a detector for detecting that the chip attaching member has been moved in the second direction with respect to the base.

6. The dispensing device of claim 5, wherein the effort applying means changes the magnitude of the effort in such a manner that the magnitude of the effort is increased in the middle of the movement in the second direction of the chip attaching member.

7. The dispensing device of claim 5, wherein the chip attaching member comprises a nozzle to which the dispensing chip is attached, a syringe pump connected to the nozzle for sucking and discharging a predetermined liquid through the dispensing chip and the nozzle, and a syringe driving source connected to the syringe pump and for driving the syringe pump.

8. The dispensing device of claim 5, further comprising:
a driving source for moving the base; and
a controller for monitoring whether or not the dispensing chip is normally attached to the chip attaching member based on an amount of driving of the driving source and an output of the detector.

9. The dispensing device of claim 8, wherein the effort applying means changes the magnitude of the effort when the chip attaching member is moved a first distance in the second direction with respect to the base,
the detector detects that the chip attaching member has been moved the first distance in the second direction with respect to the base, and detects that the chip attaching member has been moved a second distance greater than the first distance in the second direction with respect to the base,
the controller is configured to monitor the attachment of the dispensing chip to the chip attaching member based on the amount of driving of the driving source and the output of the detector when the chip attaching member has been moved the first distance and an output of the detector when the chip attaching member has been moved the second distance in the second direction with respect to the base.

10. The dispensing device of claim 5, wherein the effort applying means is configured to increase the magnitude of the effort in the middle of the moving range of the chip attaching means with respect to the base.

* * * * *